United States Patent [19]
Sugihara

[11] Patent Number: 5,848,116
[45] Date of Patent: Dec. 8, 1998

[54] X-RAY DETECTION APPARATUS

[75] Inventor: Naoki Sugihara, Otawara, Japan

[73] Assignee: Kabushiki Kaisha Toshiba, Kawasaki, Japan

[21] Appl. No.: 744,216

[22] Filed: Nov. 5, 1996

[30] Foreign Application Priority Data

Nov. 7, 1995 [JP] Japan .................................. 7-288672

[51] Int. Cl.⁶ .................................................. A61B 6/03
[52] U.S. Cl. .................................................. 378/19; 378/4
[58] Field of Search .................... 378/4, 15, 19, 378/91, 204; 256/370.09

[56] References Cited

U.S. PATENT DOCUMENTS

| | | | |
|---|---|---|---|
| 4,161,655 | 7/1979 | Cotic et al. | 378/19 X |
| 4,181,856 | 1/1980 | Bone | 378/19 X |
| 4,260,891 | 4/1981 | Williams . | |
| 4,303,863 | 12/1981 | Racz et al. | 378/19 X |
| 4,338,521 | 7/1982 | Shaw et al. | 250/370.09 X |
| 4,845,731 | 7/1989 | Vidmar et al. | 378/19 X |
| 5,323,439 | 6/1994 | Nobuta et al. | 378/19 |
| 5,444,752 | 8/1995 | Dobbs et al. | 378/19 |
| 5,487,098 | 1/1996 | Dobbs et al. | 378/19 |
| 5,499,281 | 3/1996 | Weedon et al. | 378/19 |

*Primary Examiner*—David P. Porta
*Attorney, Agent, or Firm*—Oblon, Spivak, McClelland, Maier & Neustadt, P.C.

[57] ABSTRACT

An X-ray CT apparatus comprises an X-ray tube for irradiating X-ray onto a target object, a xenon gas type detector for detecting the X-ray passing through the target object and for outputting an analog electric signal corresponding to an amount of the X-ray, a data acquisition system, a substrate for supporting the detector and the data acquisition system, which has a high rigidity and a surface where a wiring portion for transmitting an analog signal outputted from the detector to the data acquisition system is formed, and a rotation mechanism for rotating the X-ray source and the substrate for supporting the detector and the data acquisition system around the body axis of the target object as the rotation center.

13 Claims, 3 Drawing Sheets

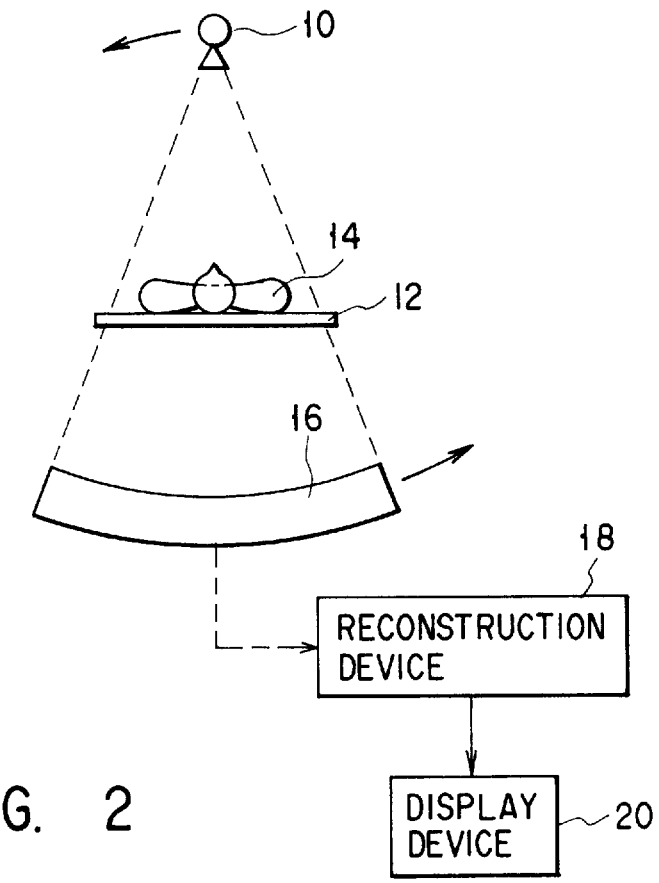
F I G. 2

X-RAY DETECTION APPARATUS

BACKGROUND OF THE INVENTION

1. Field of the Invention

The present invention relates to an X-ray detection apparatus used for an X-ray computed tomography apparatus.

2. Description of the Related Art

As for an X-ray detection apparatus, a scintillation detection apparatus and a xenon gas type detection apparatus have been put into practice. Each of these apparatus comprises an X-ray detector for detecting an X-ray which has passed through a target object and for converting a transmitted X-ray into a charge signal, and a data acquisition system (which will be abbreviated as a DAS hereinafter) for converting a detected charge signal outputted from this X-ray detector into a digital signal and for supplying a digital signal to a data reconstruction computer. The DAS comprises a front-end-processing section including an integrating circuit for processing an analog detection signal, a low-pass filter, a multiplexer, and the like, and an A/D converter for converting an analog signal outputted from the front-end-processing section, into a digital signal.

In a conventional X-ray detection apparatus, the X-ray detector and the DAS have large sizes and are respectively contained in different boxes.

FIG. 1 shows the structure of an X-ray detection apparatus used in a conventional X-ray CT apparatus. The detection apparatus comprises an X-ray detector 101 and a DAS 100, as has been described above. The DAS comprises, for example, a front-end section 106 comprising an integrating circuit and a low-pass filter, an A/D converter 104, and a control circuit 105 for controlling the front-end section 106 and the A/D converter 104. The DAS 100 is formed on one circuit board or on a plurality of circuit boards, and the circuit board or boards are contained in one box, constituting an independent apparatus.

In order to transmit a detection signal outputted from the X-ray detector 101 to the DAS 100, the X-ray detector 101 and the DAS 100 (e.g., the front end section 106 thereof) are connected with each other by a cable (such as a coaxial cable) or a vinyl-sheet type circuit board (or a flexible circuit board).

Another example of a conventional apparatus will be an apparatus in which a part of the DAS 100 is included in the X-ray detector 101. The front-end section 106 of the DAS 100 is included in the X-ray detector 101, or the front-end section 106 is divided into a first stage 102 and a second stage 103 of the front-end section. Only the first stage 102 of the front end section 106 is included in the X-ray detector 101, and the DAS 100 includes the A/D converter 104 and the controller 105 for controlling the A/D converter 104 on the basis of a timing signal used for taking in a signal outputted from the X-ray detector 101.

In this example, the first stage 102 and the second stage 103 of the front-end section or the second stage 103 and the A/D converter 104 are connected with each other by a cable or by a vinyl-sheet-like circuit board.

In any of the above examples, the X-ray detector 101 and the DAS 100 are respectively constructed as separate devices, and are electrically connected with each other by a cable or by a vinyl-sheet-like circuit board after the X-ray detector 101 and the DAS 100 are installed on a rotation gantry of the X-ray CT apparatus. In case where an X-ray detector and a DAS are constructed as separate devices, connection between both of these devices leads to the following drawback. In an X-ray CT apparatus, data is collected while rotating an X-ray tube and a detector. The rotation of the detector and the X-ray tube causes vibration of a cable or vinyl-sheet-like circuit board connected between the X-ray detector and the DAS. When the cable or the flexible circuit board for transmitting a signal vibrates, the coating film (made of resin) of the cable and the core wire (made of metal) thereof rub each other, or the circuit board (made of resin) and the printed wiring (made of metal) rub each other, thereby generating static electricity. This results in a problem that the static electricity enters as noise into an analog signal outputted from the X-ray detector 101, or into an analog signal processed by the front-end section 106. If a noise signal thus enters, there is a drawback that the image quality of a tomographic image finally reconstructed is deteriorated.

SUMMARY OF THE INVENTION

Accordingly, it is an object of the present invention to provide an X-ray detection apparatus which comprises an X-ray detector and a data processing section for converting an analog output of the X-ray detector into a digital signal and which prevents a noise signal caused by vibration of the X-ray detector from entering into the analog output signal from the X-ray detector.

According to the present invention, there is provided an X-ray detection apparatus comprising an X-ray detector for detecting X-ray and for outputting an analog signal corresponding to an amount of the X-ray detected, a data processor for converting the analog signal outputted from the X-ray detector into a digital signal, a substrate having a high rigidity, for supporting the X-ray detector and the data processor, and connection means formed on the substrate, for transmitting a signal outputted from the X-ray detector to the data processor.

According to the present invention, there is provided another X-ray computer tomography apparatus comprising irradiation means for irradiating X-ray onto a target object, detection means for detecting the X-ray passing through the target object, and for outputting an electric signal corresponding to an amount of the X-ray detected, and rotation means for rotating the irradiation means and the detection means around a body axis of the target object as a rotation center, wherein the detection means comprises an X-ray detector for detecting the X-ray and for outputting an analog signal corresponding to an amount of the X-ray detected, a data processor for converting the analog signal outputted from the X-ray detector into a digital signal, and a substrate for supporting the X-ray detector and the data processor, the substrate having a high rigidity and having a surface on which a wiring section for transmitting the signal outputted from the X-ray detector to the data processor is formed.

According to the X-ray detection apparatus of the present invention, the X-ray detector and the data processor are formed on the substrate having a high rigidity, and both of the detector and the data processor are formed to be integral with each other. Signal transmission from the detector to the data processor is achieved by a wiring formed on the substrate having the high rigidity. Therefore, the substrate does not vibrate even when the detection apparatus is rotated. As a result, static electricity which will be caused by a friction between a metal portion of a signal transmission line and a coating portion thereof does not enter into an analog signal of the detector.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 is a view schematically showing the X-ray CT apparatus in which an X-ray detection according to an embodiment of the present invention is used;

DETAILED DESCRIPTION OF THE PREFERRED EMBODIMENTS

Figure 1:
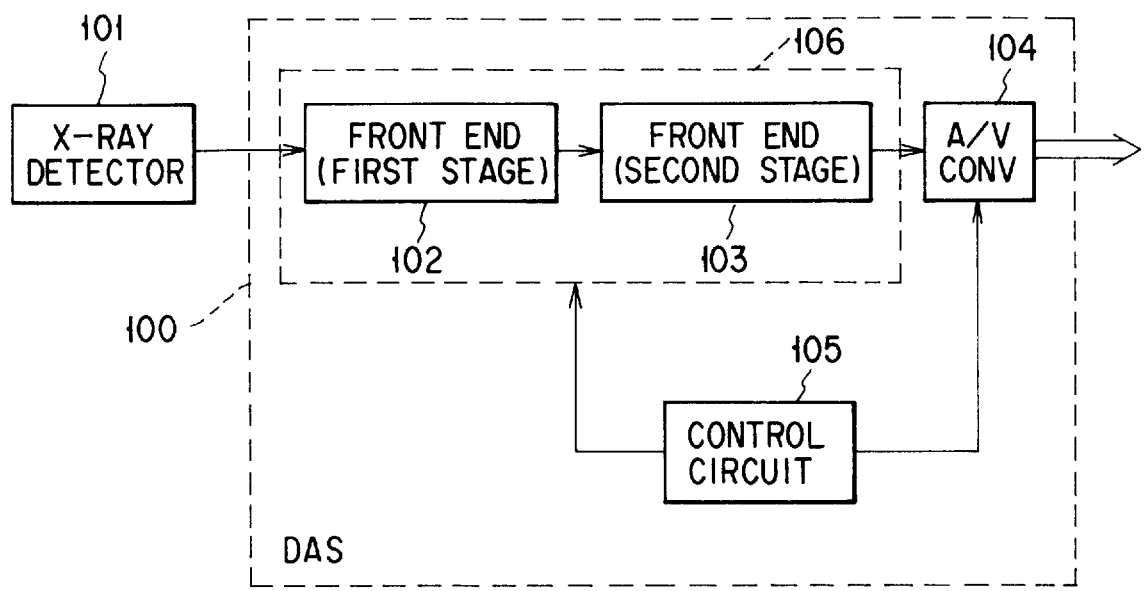
FIG. 1 is a block diagram showing a structure of an X-ray detection apparatus of a conventional X-ray CT apparatus.

A preferred embodiment of an X-ray detection apparatus according to the present invention will now be described with reference to the accompanying drawings. FIG. 2 schematically shows the entire X-ray CT apparatus of a third generation using an X-ray detection apparatus according to the present embodiment. An X-ray fan beam emitted from the X-ray tube 10 with a predetermined fan angle passes through a patient 14 laid on a bed 12 and enters into an X-ray detection apparatus 16. Projection data is thereby collected. The projection data outputted from the detection apparatus 16 is supplied to a reconstruction device 18 through a signal transmitting member such as a slip-ring or the like. The X-ray tube 10 and the X-ray detection apparatus 16 are integrally rotated by a support/rotate mechanism not shown. In this manner, projection data projected to a certain slice of the patient 14 from all directions of 360 degrees is collected, and the reconstruction device 18 reconstructs a tomographic image of one slice on the basis of the projection data, to display the tomographic image on a display device 20. In recent years, helical scanning has been put into practical use, for the purpose of reducing the scanning time. In the helical scanning, a bed 12 is moved at the same time when the X-ray tube 10 and the X-ray detection apparatus 16 are rotated, and data of a plurality of slices is sequentially collected.

Figure 3:
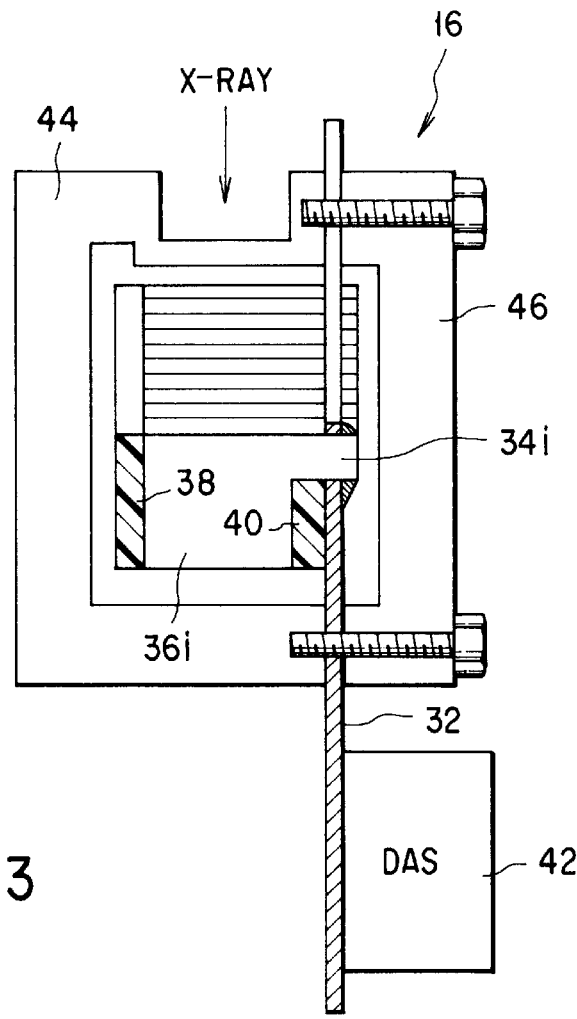
FIG. 3 is a side cross-sectional view showing the inner structure of the X-ray detection apparatus according to the embodiment of the present invention.
Figure 4:
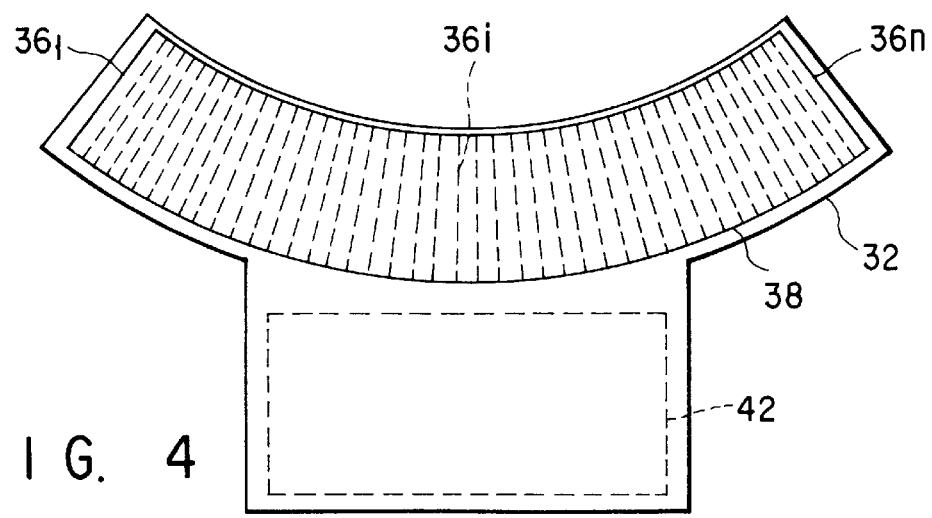
FIG. 4 is a front view showing the inner structure of the X-ray detection apparatus according to the embodiment of the present invention.

The details of the X-ray detection apparatus 16 will be explained. FIG. 3 is a cross-sectional view of the X-ray detection apparatus 16, taken from the side surface (in the lateral direction of FIG. 2). FIG. 4 is a front view of the inside, taken from the left side of FIG. 3. Each of the components of the detection apparatus 16 is installed on a circuit board 32 having a shape as shown in FIG. 4. This circuit board 32 is made of material (or synthetic resin) having a high rigidity and is a so-called printed circuit board, unlike the flexible circuit board used in a conventional apparatus. As a detector, a xenon gas type detector is used in which electrode plates are disposed at a predetermined interval. The electrode plates $36i$ (i=1 to n) are disposed in an arc-like arrangement, such that the directions of the surfaces of the plates coincide with the center of the X-ray tube 10. At a corner portion of each electrode plate $36i$, a projecting portion $34i$ as a signal extraction electrode. Both sides of each electrode plates $36i$ are fixed by resin plates 38 and 40, thus constituting a detector. Adjacent two electrode plates constituted a detector of one-channel.

After a detector is thus constructed, the resin plate 40 is fixed to one surface of the circuit board 32 by an adhesion or mechanically by a screw. The electrodes $34i$ penetrate through a through hole formed in the circuit board 32 and project from the opposite surface (or the pattern formation surface). These electrodes are electrically connected to a wiring pattern formed on the pattern formation surface, by soldering. A DAS 42 is provided on the pattern formation surface, and the wiring pattern connects the electrodes $34i$ with input terminals of channels of the DAS 42, respectively.

The circuit board 32 comprises an upper section of a sectorial shape for fixing the X-ray detector (e.g., the resin plate 40) and a lower section for fixing the DAS 42, as shown in FIG. 4. The detector is contained in a casing 44, and is sealed by a cover 46 with the circuit board 32 interposed therebetween, in order to fill the detector with a xenon gas. Note that the side of the casing 44 facing the X-ray tube 10 is thin, and serves as an X-ray entrance port.

Figure 5:
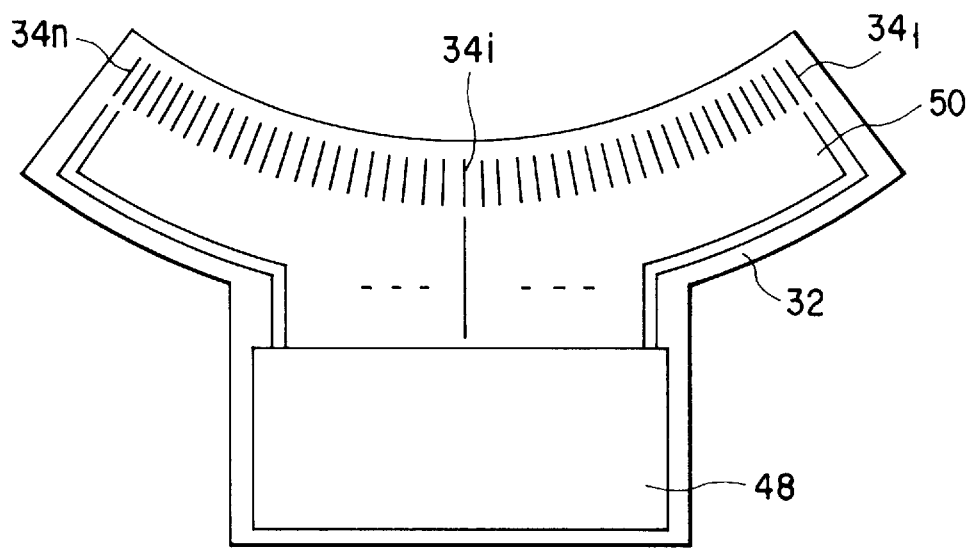
FIG. 5 is a rear view showing the inner structure of the X-ray detection apparatus according to the embodiment of the present invention.

The DAS 42 includes a front-end section including an integration circuit and a low-pass filter, an A/D (analog/digital) converter, and the like, as shown in FIG. 1. The DAS 42 is contained in a casing different from the detector. As shown in the rear view of FIG. 5, a circuit pattern 48 for the DAS 42 is formed at a lower portion of the pattern formation surface of the circuit board 32, and is electrically connected through a connector or the like, with the wiring pattern 50 connected to the electrodes $34i$ of the X-ray detector. Circuits (or electric components) of the DAS are directly installed on the circuit pattern 48.

Thus, according to the X-ray detection apparatus of the present embodiment, the X-ray detector and the DAS 48 are fixed onto the circuit board 32 having a high rigidity so that the X-ray detector and the DAS 48 are integrated with each other. Therefore, when the X-ray detection apparatus 16 is rotated together with the X-ray tube 10 are rotated around the body axis of a target object to collect projection data, the X-ray detector, the circuit board 32, and the DAS 42 integrally vibrate. Therefore, connecting portions between the X-ray detector 16 and the printed wiring pattern on the circuit board 32 and between the DAS 42 and this printed wiring pattern are not broken due to vibration, but a high reliability is ensured. Further, since the wiring pattern is formed on a circuit board having a high rigidity, the circuit board (made of resin) and the printed wiring (made of metal) do not rub each other, so that there is no static electricity caused by friction. As a result, the X-ray detection apparatus according to the present embodiment overcomes the drawback of a conventional apparatus that static electricity enters as noise into an analog electric signal outputted from the X-ray detector or an analog electric signal processed by the DAS. Accordingly, the image quality of a tomographic image finally reconstructed is not damaged.

Note that a digital output of the DAS 42 is fed to the slip ring through a cable, a flexible circuit board, or the like, and is supplied to the reconstruction device 18 shown in FIG. 2. Since the signal which is transmitted through the cable is a digital signal, electrostatic noise does not enter into the digital signal.

As has been described above, according to the present embodiment, there is provided an X-ray detection apparatus into which electrostatic noise does not enter even when vibration occurs.

Another embodiment of the present invention will be explained. In the following embodiment, the same portions as used in the first embodiment will be denoted by the same reference numerals, and detailed explanation of those portions will be omitted therefrom.

Figure 6:
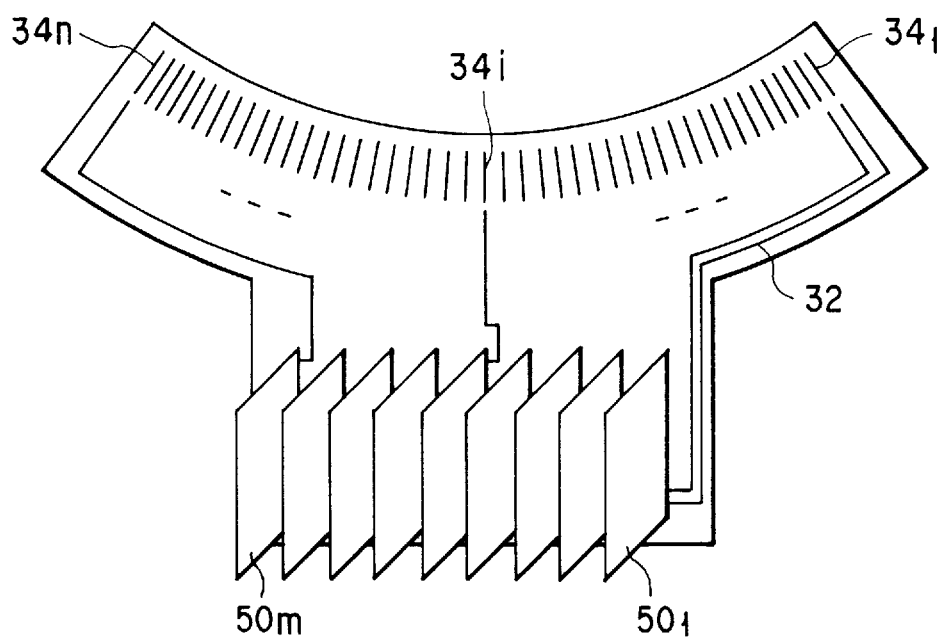
FIG. 6 is a rear view showing the inner structure of another embodiment of the present invention.

In the first embodiment, the circuit pattern 48 for the DAS 42 is formed directly on the circuit board 32. However, if the circuit pattern is of a large scale, the circuit board 32 must undesirably be of a large scale. In this case, the DAS 42 may be divided into several sections, which may respectively be formed on circuit boards 50$j$ (j=1 to m). These circuit boards 50$j$ may be fixed vertically on the circuit board 32 and may be connected to a connector provided on the wiring pattern formed on the circuit board, as shown in FIG. 6. In this manner, the area of the circuit board 32 can be reduced and the size of the entire apparatus is reduced.

As has been explained above, according to the present invention, there is provided an X-ray detection apparatus which prevents electrostatic noise caused by vibration of the X-ray detector from entering into an analog electric signal outputted from the X-ray detector.

The present invention is not limited to the embodiment described above, but may be variously modified in practice. For example, the DAS which is provided on the circuit board opposite to the detector may be provided in the same side as the detector is provided. In this case, an end of the wiring pattern formed on the pattern formation surface is connected through a through-hole to the side of the DAS opposite to the pattern formation surface. In the above description, the xenon gas type detector is explained as an detector. The detector is not limited to the above type but any type of detector, e.g., a solid-state detector may be used.

What is claimed is:

1. An X-ray detection apparatus comprising:
   an X-ray detector for detecting an X-ray and for outputting an analog signal corresponding to an amount of the X-ray detected, said X-ray detector including a casing with a cover for sealing in a gas component of the X-ray detector;
   a data processor for converting the analog signal outputted from said X-ray detector into a digital signal;
   a substrate having a high rigidity, said substrate having a data processor circuit pattern on a first portion mounting said data processor, a second portion mounting said X-ray detector and a third portion providing connecting wiring between said X-ray detector and said data processor, said connecting wiring transmitting a signal outputted from said X-ray detector to said data processor; and
   wherein said second portion of the substrate is interposed between said casing and said sealing cover.

2. The apparatus according to claim 1, wherein said substrate comprises a printed circuit board made of rigid resin, said printed circuit board including printed wiring as said connecting wiring and said data processor circuit pattern.

3. The apparatus according to claim 1, wherein said gas component comprises xenon gas, said X-ray detector and said data processor are respectively provided on opposite surfaces of said substrate, and a signal output electrode of said X-ray detector is connected through a through-hole provided in said substrate to a surface of said substrate on which said data processor is mounted.

4. The apparatus according to claim 3, wherein said first portion of said substrate mounting said data processor is provided outside the casing.

5. An X-ray computer tomography apparatus comprising:
   irradiation means for irradiating an X-ray onto a target object;
   detection means for detecting the X-ray passing through the target object and for outputting an electric signal corresponding to an amount of the X-ray detected;
   wherein said detection means comprises an X-ray detector for detecting the X-ray and for outputting an analog signal corresponding to an amount of the X-ray detected, said X-ray detector including a casing with a cover for sealing in a gas component of the X-ray detector, a data processor for converting the analog signal outputted from said X-ray detector into a digital signal, and a substrate having a data processor circuit pattern on a first portion mounting said data processor, a second portion mounting said X-ray detector and interposed between said casing and said sealing cover, and a third portion providing connecting wiring to connect said X-ray detector to said data processor, said substrate having a high rigidity; and
   rotation means for rotating said irradiation means and said detection means around an axis of the target object serving as a center of rotation.

6. The apparatus according to claim 5, wherein said substrate comprises a printed circuit board made of rigid resin.

7. The apparatus according to claim 5, wherein said gas component comprises xenon gas, said X-ray detector and said data processor are respectively provided on opposite surfaces of said substrate, and a signal output electrode of said X-ray detector is connected through a through hole provided in said substrate to a surface of said substrate on which said data processor is mounted.

8. The apparatus according to claim 7, wherein said X-ray detector includes a number of electrode plates arranged to extend at right angles to said substrate and disposed such that extending directions of surfaces of the electrode plates correspond to an irradiation center of said irradiation means, said electrode plates each having a part connected through the through hole of said substrate to the connecting wiring on the surface of said substrate which is opposite to the surface where said X-ray detector is mounted.

9. The apparatus according to claim 5, wherein said first portion of said substrate mounting said data processor is provided outside of the casing.

10. The apparatus according claim 5, further comprising:
    a bed on which the target object is laid; and
    moving means for moving the bed in a direction of a longitudinal axis of the target object, while said rotation means rotates said irradiation means and said detection means around said target object.

11. The apparatus according to claim 5, wherein said data processor includes an integration circuit, a lowpass filter, and an analog/digital converter.

12. The apparatus according to claim 5, wherein said data processor comprises circuit components connected to the circuit pattern formed on said substrate.

13. An X-ray computer tomography apparatus according to claim 5, wherein said data processor comprises a plurality of circuit sections, each of the circuit sections being respectively formed on circuit boards, and each of said circuit boards being arranged on said substrate in a direction crossing a longitudinal dimension of said substrate, with one of said plurality of circuit sections being an analog to digital converter section; and rotating means for rotating said irradiation means and said detection means around an axis of the target object serving as a center of rotation.

\* \* \* \* \*